(12) United States Patent
Laurent et al.

(10) Patent No.: US 11,339,320 B2
(45) Date of Patent: May 24, 2022

(54) THIOL-FORMYL HEMIACETAL CORROSION INHIBITORS

(71) Applicant: ChampionX USA Inc., Sugarland, TX (US)

(72) Inventors: Boyd Anthony Laurent, Pearland, TX (US); Prakasa Rao Anantaneni, Richmond, TX (US); Ryan Matthew Harrington, Houston, TX (US); Subhasis De, Webster, TX (US)

(73) Assignee: ChampionX USA Inc., Sugar Land, TX (US)

( * ) Notice: Subject to any disclaimer, the term of this patent is extended or adjusted under 35 U.S.C. 154(b) by 3 days.

(21) Appl. No.: 15/829,576

(22) Filed: Dec. 1, 2017

(65) Prior Publication Data

US 2018/0155609 A1 Jun. 7, 2018
US 2018/0346795 A9 Dec. 6, 2018

Related U.S. Application Data

(60) Provisional application No. 62/429,507, filed on Dec. 2, 2016.

(51) Int. Cl.
| | | |
|---|---|---|
| *C09K 8/54* | (2006.01) | |
| *C09K 15/12* | (2006.01) | |
| *C07C 323/25* | (2006.01) | |
| *C07C 323/52* | (2006.01) | |
| *C07C 323/12* | (2006.01) | |

(52) U.S. Cl.
CPC .............. *C09K 8/54* (2013.01); *C07C 323/12* (2013.01); *C07C 323/25* (2013.01); *C07C 323/52* (2013.01); *C09K 15/12* (2013.01); *C09K 2208/32* (2013.01)

(58) Field of Classification Search
CPC .... C09K 2208/32; C09K 8/528; C09K 8/685; C09K 8/887; C09K 15/12; C09K 2208/10; C09K 8/03; C09K 8/467; C09K 8/524; C09K 8/54; C09K 8/62; C09K 8/64; C09K 8/72; C09K 8/74; C09K 8/80; C09K 8/805; C09K 8/82; C09K 8/90; C09K 8/92; C09K 8/00; E21B 37/06; E21B 43/04; E21B 43/267; E21B 43/26; E21B 47/1015; E21B 49/08
See application file for complete search history.

(56) References Cited

U.S. PATENT DOCUMENTS

| | | | | |
|---|---|---|---|---|
| 2,998,462 | A * | 8/1961 | Crabb | C07C 21/12 252/364 |
| 3,763,048 | A * | 10/1973 | Nishihara | C07C 17/42 570/120 |
| 4,000,079 | A | 12/1976 | Rasp et al. | |
| 4,633,019 | A * | 12/1986 | Thompson | C07C 323/25 564/1 |
| 6,365,067 | B1 | 4/2002 | Ahn et al. | |
| 6,645,399 | B2 | 11/2003 | Ahn et al. | |
| 7,216,710 | B2 | 5/2007 | Welton et al. | |
| 9,238,588 | B2 | 1/2016 | Harrington et al. | |
| 2005/0169794 | A1* | 8/2005 | Welton | C09K 8/74 422/15 |
| 2014/0216748 | A1 | 8/2014 | Pou | |
| 2014/0343332 | A1 | 11/2014 | Pou et al. | |
| 2015/0037202 | A1* | 2/2015 | Harrington | C09K 8/54 422/7 |
| 2016/0090655 | A1 | 3/2016 | Pou et al. | |
| 2016/0230078 | A1 | 8/2016 | Pou et al. | |
| 2019/0112717 | A1* | 4/2019 | Mohr | C23G 1/19 |

FOREIGN PATENT DOCUMENTS

| | | | |
|---|---|---|---|
| CN | 102321464 | * | 1/2012 |
| CN | 105418509 | A | 3/2016 |
| FR | 2761083 | A1 | 9/1998 |
| JP | H10140379 | * | 5/1998 |
| WO | 2005/075707 | A1 | 8/2005 |
| WO | 2010/119235 | A1 | 10/2010 |
| WO | 2015/017385 | A2 | 2/2015 |
| WO | 2016/089459 | A1 | 6/2016 |

OTHER PUBLICATIONS https://scifinder.cas.org/scifinder/view/scifinder/scifinderExplore.jsf dated Dec. 18, 2019.*
Gao et al, Study on tribological properties of 2,5-dialkoxymethylthio-1,3,4-thiadiazoles, Wear 222, 1998, 129-134.*
Gohar, C.A. et al. Some [(substituted benzylidene)dithio]diacetic acid as inhibitors for the acidic corrosion of aluminum, Bulletin of Electrochemistry, 10, 1994, 433-438.*
Brahim, I. M., et al., "Relative Performance of Isopropylamine, Pyrrole and Pyridine as Corrosion Inhibitors for Carbon Steels in Saline Water at Mildly Elevated Temperatures," International Journal of Scientific & Engineering Research, Feb. 2013, pp. 1-12, vol. 4, No. 2.
Zhou, S.-L., et al., "Two Compounds from the Endophytic *Colletotrichum* sp. of Ginkgo biloba," Natural Product Communications, Aug. 2011, pp. 1131-1132, vol. 6, No. 8.
Fujioka, H., et al., "Organic Chemistry Using Weakly Electrophilic Salts: Efficient Formation of O,O-Mixed, O,S- and N,O-Acetals," The Journal of Organic Chemistry, 2007, pp. 7898-7902, vol. 72, No. 21.
International Search Report and Written Opinion issued for PCT/US2017/064282, dated May 7, 2018, 20 pages.
Li, J.-X., et al., "Characterization of the Major Odor-Active Compounds in Thai Durian (Durio zibethinus L. 'Monthong') by Aroma Extract Dilution Analysis and Headspace Gas Chromatography-Olfactomery," Journal of Agricultural and Food Chemistry, 2012, pp. 11253-11262, vol. 60, No. 45.

\* cited by examiner

*Primary Examiner* — Kumar R Bhushan
(74) *Attorney, Agent, or Firm* — Stinson LLP

(57) ABSTRACT

The present invention generally relates to compositions and methods for inhibiting corrosion at a surface in the production, transportation, storage, and separation of crude oil and natural gas.

19 Claims, No Drawings

THIOL-FORMYL HEMIACETAL CORROSION INHIBITORS

CROSS REFERENCE TO RELATED APPLICATIONS

This application claims the benefit of U.S. Provisional Patent Application Ser. No. 62/429,507 filed on Dec. 2, 2016, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

STATEMENT REGARDING PRIOR DISCLOSURES BY THE INVENTOR OR JOINT INVENTORS

Not applicable.

FIELD OF THE INVENTION

Compositions for inhibiting corrosion are provided, as well as their preparation and use in methods for inhibiting corrosion at a surface in the production, transportation, storage, and separation of crude oil and natural gas.

BACKGROUND OF THE INVENTION

One of the greatest risks to oil and gas production infrastructure is accelerated internal pipeline corrosion, particularly as a field ages and water cut rises. The production of oil and gas reservoirs present corrosive environments that place the internal metallurgy of process equipment (e.g., transport pipelines, flow lines, separation equipment), often constructed of mild carbon steel, at risk for failure. The rate of corrosion deterioration in oil and gas field equipment metallurgy is dependent upon production parameters such as oil/water ratio, fluid brine composition, temperature, pH, and the concentration of corrosive gases typically present in the reservoir formation, such as $CO_2$, $H_2S$, or combinations thereof.

In order to preserve the integrity of oil and gas infrastructure, corrosion inhibitors are typically added into the production fluids upstream of piping infrastructure intended to be protected. In general, corrosion inhibitors of this type protect the metal through formation of a passivation film on the metal surface. This passivation layer oil wets the metal surface, which in turn prevents contact of the metal from the corrosive nature of the produced reservoir fluids. Typically, corrosion inhibitor formulations of this type contain a variety of aliphatic organic surfactant molecules ranging from, but not limited to, amines, quaternary amines, imidazolines, phosphate esters, amides, carboxylic acids, or combinations thereof.

Often, organic thiol compounds are added in low concentrations to these corrosion inhibitor components to increase the effectiveness of the traditional corrosion inhibitor molecules. It is believed that these organic thiol molecules create a stronger passivation layer on the metal surface which also increases the persistency of the protective film. In most examples, the sulfur based component consists of a primary thio/mercaptan (e.g., 2-mercaptoethanol or mercaptoacetic acid). In some instances, however, such thiol based formulations can degrade at elevated temperatures (e.g., during storage at elevated temperatures) to release volatile sulfur-containing vapor/gases (e.g., mercaptans, sulfur dioxide, hydrogen sulfide, and/or carbonyl sulfide).

These volatile sulfur-containing gases are likely created by decomposition of the sulfur-based derivatives, and probably thioglycolic acid, mercaptoalcohols, and the like, decompose to product hydrogen sulfide. This decomposition is a source of environmental and safety problems making the corrosion inhibitors including such sulfur compounds difficult to handle and use.

Thus, despite the availability of corrosion inhibitors for use in the oil and gas industry, there still exists a need for improved compounds, compositions, and methods having reduced toxicity and greater ease of handling.

BRIEF SUMMARY OF THE INVENTION

A method of inhibiting corrosion at a surface is provided. The method comprising contacting the surface with an anti-corrosion composition comprising a compound of formula (I)

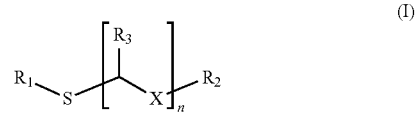
(I)

wherein $R_1$ is alkyl, aryl, alkenyl, heterocyclo, or $R_1$ and $R_2$ together with the sulfur, carbon, and oxygen atoms form a ring; n is an integer from 1 to 10; $R_2$ is hydrogen, alkyl, alkenyl, aryl, or $R_1$ and $R_2$ together with the sulfur, carbon, and X groups form a ring; $R_3$ is hydrogen, alkyl, alkaryl, aryl, or heterocyclo; X is —O—, —S—, or —$NR_5$; and $R_5$ is hydrogen, alkyl, alkenyl, aryl, or $R_1$ and $R_5$ together with the sulfur, carbon, and nitrogen form a ring.

Use of an anti-corrosion composition comprising the compound of formula (I) to inhibit corrosion at a surface is provided.

A method of inhibiting corrosion at a surface contacting the surface with an anti-corrosion composition or use of an anti-corrosion composition to inhibit corrosion at a surface, the anti-corrosion composition comprising a compound of formula (IA)

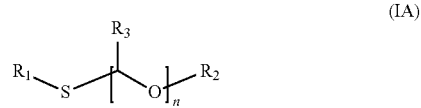
(IA)

wherein $R_1$ is alkyl, aryl, alkenyl, heterocyclo; n is an integer from 1 to 10; $R_2$ is hydrogen; and $R_3$ is hydrogen, alkyl, or aryl.

Yet another aspect of the invention is a method of inhibiting corrosion at a surface contacting the surface with an anti-corrosion composition or use of an anti-corrosion composition to inhibit corrosion at a surface, the anti-corrosion composition comprising a compound of formula (IB)

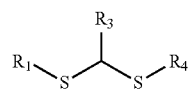

(IB)

wherein $R_1$ is alkyl, aryl, alkenyl, or heterocyclo; $R_3$ is hydrogen, alkyl, alkaryl, aryl, or heterocyclo; and $R_4$ is alkyl, aryl, alkenyl, or heterocyclo.

Another aspect of the invention is a method of inhibiting corrosion at a surface. The method comprising contacting the surface with an anti-corrosion composition comprising a compound of formula (II)

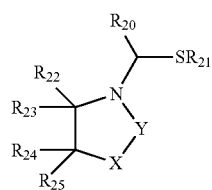

(II)

wherein $R_{20}$ is hydrogen, alkyl, aryl, alkenyl, or heterocyclo; $R_{21}$ is alkyl, aryl, alkenyl, or heterocyclo; $R_{22}$ and $R_{25}$ are independently hydrogen, alkyl, aryl, or together with the carbon atoms they are attached to form a fused ring; $R_{23}$ and $R_{24}$ are hydrogen, combine to form a double bond between the carbon atoms, or when $R_{22}$ and $R_{25}$ form a fused ring, $R_{23}$ and $R_{24}$ form a double bond between the carbon atoms; Y is —$CR_{26}R_{27}$—, —$CR_{26}R_{27}CR_{26}R_{27}$—, —C(O)—, —C(S)—, —$S(O_2)$—; X is —$CR_{28}R_{29}$—, —O—, —S—, —$NR_{30}$—, —$N(C(R_{20})SR_{21})$—; and $R_{26}$, $R_{27}$, $R_{28}$, $R_{29}$, and $R_{30}$ are independently hydrogen, alkyl, or aryl.

Yet another aspect of the invention is use of an anti-corrosion composition to inhibit corrosion at a surface, the anti-corrosion composition comprising the compound of formula (II).

A further aspect of the invention is a method of inhibiting corrosion at a surface. The method comprising contacting the surface with an anti-corrosion composition comprising a compound of formula (III)

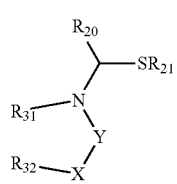

(III)

wherein $R_{20}$ is hydrogen, alkyl, aryl, alkenyl, or heterocyclo; $R_{21}$ is alkyl, aryl, alkenyl, or heterocyclo; Y is —$CR_{26}R_{27}$—, —$CR_{26}R_{27}CR_{26}R_{27}$—, —C(O)—, —C(S)—, —$S(O_2)$—; X is —$CR_{28}R_{29}$—, —O—, —S—, —$NR_{30}$—, —$N(C(R_{20})SR_{21})$—; $R_{26}$, $R_{27}$, $R_{28}$, $R_{29}$, and $R_{30}$ are independently hydrogen, alkyl, or aryl; and $R_{31}$ and $R_{32}$ are alkyl, alkenyl, alkynyl, or aryl.

Yet a further aspect of the invention is use of an anti-corrosion composition to inhibit corrosion at a surface, the anti-corrosion composition comprising the compound of formula (III).

A further aspect of the invention is a method of inhibiting corrosion at a surface. The method comprising contacting the surface with an anti-corrosion composition comprising a compound of formula (IV)

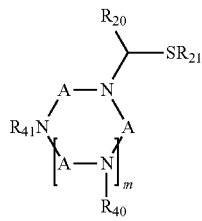

(IV)

wherein $R_{20}$ is hydrogen, alkyl, aryl, alkenyl, or heterocyclo; $R_{21}$ is alkyl, aryl, alkenyl, or heterocyclo; A is —$CR_{26}R_{27}$—, —$(CR_{26}R_{27})_2$—, —$(CR_{26}R_{27})_3$—, —$(CR_{26}R_{27})_4$—; and $R_{40}$ and $R_{41}$ are independently hydrogen, alkyl, —$C(R_{20})SR_{21}$.

Yet another aspect of the invention is use of an anti-corrosion composition to inhibit corrosion at a surface, the anti-corrosion composition comprising the compound of formula (IV).

Another aspect of the invention is a method of reducing the amount of hydrogen sulfide or mercaptans in a hydrocarbon fluid comprising contacting the hydrocarbon fluid with an effective amount of a composition comprising a compound of formula (IA)

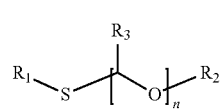

(IA)

wherein $R_1$ is alkyl, aryl, alkenyl, heterocyclo; n is an integer from 2 to 10; $R_2$ is hydrogen; and $R_3$ is hydrogen, alkyl, or aryl.

Yet another aspect of the invention are the compounds of formulae (I), (IA), (IB), (II), (III) and (IV).

Anti-corrosion compositions comprising the compound of formula (I), (IA), (IB), (II), (III) or (IV) are also provided.

Other objects and features will be in part apparent and in part pointed out hereinafter.

BRIEF DESCRIPTION OF THE SEVERAL VIEWS OF THE DRAWING

Not applicable.

DETAILED DESCRIPTION OF THE INVENTION

Disclosed herein are corrosion inhibitor compounds and compositions, methods of using said compounds and compositions, and processes for their preparation. The compounds and compositions are particularly useful for inhibiting corrosion in equipment used in the production, transportation, storage, and separation of crude oil and natural gas. The compounds and compositions include a class of thiol-formyl hemiacetal corrosion inhibitors that are stable at elevated temperatures when contained in a blended corrosion inhibitor formulation, and show reduced or no volatile degradation species in the vapor phase, unlike that of alkylthiol based counterparts. As an added benefit, the disclosed thiol-formyl hemiacetals do not exhibit the harsh, offensive thiol/mercaptan based odor typically associated with thiol containing corrosion inhibitors.

Further, the anti-corrosion compositions of the invention can advantageously replace the sulfur-containing compounds usually present in corrosion inhibiting compositions, provide improved storage stability thereby reducing the amount of hydrogen sulfide produced upon storage.

One aspect of the invention is directed to a method of inhibiting corrosion at a surface. The method comprising contacting the surface with an anti-corrosion composition comprising a compound of formula (I)

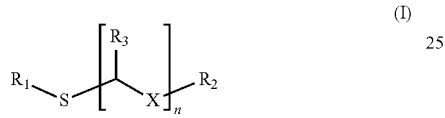

(I)

wherein $R_1$ is alkyl, aryl, alkenyl, heterocyclo, or $R_1$ and $R_2$ together with the sulfur, carbon, and oxygen atoms form a ring; n is an integer from 1 to 10; $R_2$ is hydrogen, alkyl, alkenyl, aryl, or $R_1$ and $R_2$ together with the sulfur, carbon, and X groups form a ring; $R_3$ is hydrogen, alkyl, alkaryl, aryl, or heterocyclo; X is —O—, —S—, or —$NR_5$; and $R_5$ is hydrogen, alkyl, alkenyl, aryl, or $R_1$ and $R_5$ together with the sulfur, carbon, and nitrogen form a ring.

The present invention is directed to a method of inhibiting corrosion at a surface. The method comprising contacting the surface with an anti-corrosion composition comprising a compound of formula (IA)

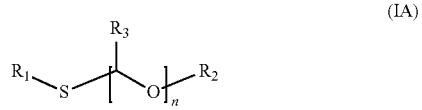

(IA)

wherein $R_1$ is alkyl, aryl, alkenyl, heterocyclo, or $R_1$ and $R_2$ together with the sulfur, carbon, and oxygen atoms form a ring; n is an integer from 1 to 10; $R_2$ is hydrogen, alkyl, alkenyl, aryl, or $R_1$ and $R_2$ together with the sulfur, carbon, and oxygen atoms form a ring; and $R_3$ is hydrogen, alkyl, alkaryl, aryl, or heterocyclo.

Another aspect of the invention is a method of reducing the amount of hydrogen sulfide or mercaptans in a hydrocarbon fluid comprising contacting the hydrocarbon fluid with an effective amount of a composition comprising a compound of formula (IA)

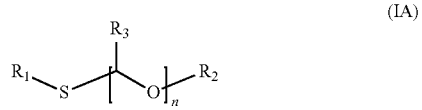

(IA)

wherein $R_1$ is alkyl, aryl, alkenyl, heterocyclo; n is an integer from 2 to 10; $R_2$ is hydrogen; and $R_3$ is hydrogen, alkyl, or aryl.

Further, for the compound of formula (IA), $R_1$ is alkyl, aryl, alkenyl, heterocyclo; n is an integer from 1 to 10; $R_2$ is hydrogen; and $R_3$ is hydrogen, alkyl, or aryl.

Another aspect of the invention is a method of inhibiting corrosion at a surface. The method comprising contacting the surface with an anti-corrosion composition comprising a compound of formula (IB)

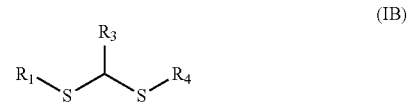

(IB)

wherein $R_1$ is alkyl, aryl, alkenyl, or heterocyclo; $R_3$ is hydrogen, alkyl, alkaryl, aryl, or heterocyclo; and $R_4$ is alkyl, aryl, alkenyl, or heterocyclo.

The anti-corrosion composition can comprise a compound of formula (IA)

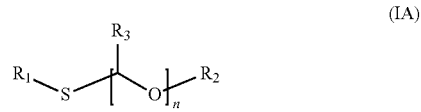

(IA)

wherein $R_1$ is alkyl, aryl, alkenyl, heterocyclo, or $R_1$ and $R_2$ together with the sulfur, carbon, and oxygen atoms form a ring; n is an integer from 1 to 10; $R_2$ is hydrogen, alkyl, alkenyl, aryl, or $R_1$ and $R_2$ together with the sulfur, carbon, and oxygen atoms form a ring; and $R_3$ is hydrogen, alkyl, alkaryl, aryl, or heterocyclo. Preferably, $R_1$ is alkyl, aryl, alkenyl, heterocyclo; n is an integer from 1 to 10; $R_2$ is hydrogen; and $R_3$ is hydrogen, alkyl, or aryl.

The anti-corrosion composition can comprise the compound of formula (IB).

The invention can further be directed to a method of inhibiting corrosion at a surface. The method comprising contacting the surface with an anti-corrosion composition comprising a compound of formula (IC)

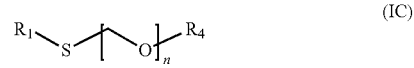

(IC)

wherein $R_1$ is alkyl, aryl, alkenyl, heterocyclo, or $R_1$ and $R_2$ together with the sulfur, carbon, and oxygen atoms form a ring; n is an integer from 1 to 10; and $R_2$ is hydrogen, alkyl, alkenyl, aryl, or $R_1$ and $R_2$ together with the sulfur, carbon, and oxygen atoms form a ring.

The invention can further be directed to an anti-corrosion composition comprising the compound of formula (IC).

The anti-corrosion composition can further exhibit increased stability to release of hydrogen sulfide upon storage as compared to an otherwise identical composition containing $R_1SH$.

The compounds of formula (I) as described herein can further exhibit increased stability to release of hydrogen sulfide upon storage as compared to a compound $R_1SH$.

The compound of formula (I) can have $R_1$ be $C_1$-$C_{24}$ alkyl, $C_1$-$C_{24}$ alkenyl, $C_6$-$C_{12}$ aryl, monocyclic or bicyclic heteroaryl, or $C_3$-$C_8$ cycloalkyl, wherein said alkyl, alkenyl, aryl, heteroaryl, or cycloalkyl are each independently unsubstituted or substituted with 1 to 3 substituents independently selected from —F, —Cl, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_{10}$ and $R_{11}$, at each occurrence, are each independently hydrogen or $C_1$-$C_6$ alkyl; or optionally one or more of the —$CH_2$— groups of $R_1$ is replaced with a —C(O)O— group.

The compound of formula (I) can have $R_1$ be $C_1$-$C_{24}$ alkyl, $C_1$-$C_{24}$ alkenyl, $C_6$-$C_{12}$ aryl, monocyclic or bicyclic heteroaryl, or $C_3$-$C_8$ cycloalkyl, wherein said alkyl, alkenyl, aryl, heteroaryl, or cycloalkyl are each independently unsubstituted or substituted with 1 to 3 substituents independently selected from —F, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_{10}$ and $R_{11}$, at each occurrence, are each independently hydrogen or $C_1$-$C_6$ alkyl; or optionally one or more of the —$CH_2$— groups of $R_1$ is replaced with a —C(O)O— group.

The compound of formula (I) can have $R_1$ be $C_1$-$C_{18}$ alkyl, or $C_3$-$C_8$ cycloalkyl, wherein said alkyl, or cycloalkyl are each independently unsubstituted or substituted with 1 to 3 substituents independently selected from —OH, $C_1$-$C_6$ alkoxy, or —$CO_2R_{10}$, wherein $R_{10}$ at each occurrence, is independently hydrogen or $C_1$-$C_6$ alkyl; or optionally one or more of the —$CH_2$— groups of $R_1$ is replaced with a —C(O)O— group.

The compound of formula (I) can have $R_1$ be $C_1$-$C_{18}$ alkyl or $C_3$-$C_8$ cycloalkyl.

The compound of formula (I) can have $R_1$ be $C_1$-$C_{18}$ alkyl.

The compound of formula (I) can have $R_1$ be $C_1$-$C_{12}$ alkyl optionally substituted with 1 to 3 substituents of —OH or —$CO_2H$; or $R_1$ is $C_1$-$C_{12}$ alkyl wherein one or more of the —$CH_2$— groups replaced with a —C(O)O— group.

The compound of formula (I) can have $R_1$ be $C_1$-$C_{12}$ alkyl substituted with 1 to 3 substituents of —OH or —$CO_2H$; or $R_1$ is $C_1$-$C_{12}$ alkyl wherein one or more of the —$CH_2$— groups is replaced with a —C(O)O— group.

The compound of formula (I) can have $R_1$ be a linear $C_1$-$C_{10}$ alkyl substituted with a terminal —OH group.

The compound of formula (I) can have $R_1$ be a linear $C_1$-$C_{10}$ alkyl wherein one of the —$CH_2$— groups is replaced with a —C(O)O— group.

The compound of formula (I) can have $R_1$ be —$CH_2$—$CH_2$—OH.

When the compound of formula (I) has $R_1$ as —$CH_2$—$CH_2$—OH, n can be from 1 to 5.

The compound of formula (I) can have $R_1$ be cyclohexyl.

The compound of formula (I) can have $R_1$ be —$(CH_2)_6$—OH.

The compound of formula (I) can have $R_1$ be propyl.

The compound of formula (I) can have $R_1$ be dodecyl.

The compound of formula (I) can have $R_1$ be —$CH_2CH(OH)CH_2OH$.

The compound of formula (I) can have $R_1$ be —$CH(C(O)OH)CH_2C(O)OH$.

The compound of formula (I) can have $R_1$ be —$(CH_2)_2C(O)OCH_2CH(C_2H_5)C_4H_9$.

The compound of formula (I) can have $R_1$ be —$(CH_2)_2C(O)OH$.

The compound of formula (I) can have $R_2$ be hydrogen.

The compound of formula (I) can have $R_1$ and $R_2$ together with the sulfur, carbon, and oxygen atoms form a ring.

The compound of formula (I) can have n be 1 to 5. Preferably, n can be 1.

The compound of formula (I) can have $R_3$ be hydrogen, alkyl, or aryl.

The compound of formula (I) can have $R_3$ be hydrogen, methyl, ethyl, propyl, or phenyl.

The compound of formula (I) can have $R_3$ be hydrogen, methyl, or phenyl. Preferably, $R_3$ can be hydrogen.

The compound of formula (IB) can have $R_4$ be $C_1$-$C_{24}$ alkyl, $C_1$-$C_{24}$ alkenyl, $C_6$-$C_{12}$ aryl, monocyclic or bicyclic heteroaryl, or $C_3$-$C_8$ cycloalkyl, wherein said alkyl, alkenyl, aryl, heteroaryl, or cycloalkyl are each independently unsubstituted or substituted with 1 to 3 substituents independently selected from —F, —Cl, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_{10}$ and $R_{11}$, at each occurrence, are each independently hydrogen or $C_1$-$C_6$ alkyl; or optionally one or more of the —$CH_2$— groups of $R_4$ is replaced with a —C(O)O— group.

The compound of formula (IB) can have $R_4$ be $C_1$-$C_{24}$ alkyl, $C_1$-$C_{24}$ alkenyl, $C_6$-$C_{12}$ aryl, monocyclic or bicyclic heteroaryl, or $C_3$-$C_8$ cycloalkyl, wherein said alkyl, alkenyl, aryl, heteroaryl, or cycloalkyl are each independently unsubstituted or substituted with 1 to 3 substituents independently selected from —F, —Cl, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_3$ and $R_4$, at each occurrence, are each independently hydrogen or $C_1$-$C_6$ alkyl; or optionally one or more of the —$CH_2$— groups of $R_4$ is replaced with a —C(O)O— group.

The compound of formula (IB) can have $R_4$ be $C_1$-$C_{18}$ alkyl, or $C_3$-$C_8$ cycloalkyl, wherein said alkyl, or cycloalkyl are each independently unsubstituted or substituted with 1 to 3 substituents independently selected from —OH, $C_1$-$C_6$ alkoxy, or —$CO_2R_{10}$, wherein $R_{10}$ at each occurrence, is independently hydrogen or $C_1$-$C_6$ alkyl; or optionally one or more of the —$CH_2$— groups of $R_4$ is replaced with a —C(O)O— group.

The compound of formula (IB) can have $R_4$ be $C_1$-$C_{18}$ alkyl or $C_3$-$C_8$ cycloalkyl.

The compound of formula (IB) can have $R_4$ be $C_1$-$C_{18}$ alkyl.

The compound of formula (IB) can have $R_4$ be $C_1$-$C_{12}$ alkyl optionally substituted with 1 to 3 substituents of —OH or —$CO_2H$; or $R_4$ is $C_1$-$C_{12}$ alkyl wherein one or more of the —$CH_2$— groups replaced with a —C(O)O— group.

The compound of formula (IB) can have $R_4$ be $C_1$-$C_{12}$ alkyl substituted with 1 to 3 substituents of —OH or —$CO_2H$; or $R_4$ is $C_1$-$C_{12}$ alkyl wherein one or more of the —$CH_2$— groups is replaced with a —C(O)O— group.

The compound of formula (IB) can have $R_4$ be a linear $C_1$-$C_{10}$ alkyl substituted with a terminal —OH group.

The compound of formula (IB) can have $R_4$ be a linear $C_1$-$C_{10}$ alkyl wherein one of the —$CH_2$— groups is replaced with a —C(O)O— group.

The compound of formula (IB) can have $R_4$ be —$CH_2$—$CH_2$—OH.

The compound of formula (IB) can have $R_4$ be cyclohexyl.

The compound of formula (IB) can have $R_4$ be —$(CH_2)_6$—OH.

The compound of formula (IB) can have $R_4$ be propyl.

The compound of formula (IB) can have $R_4$ be dodecyl.

The compound of formula (IB) can have $R_4$ be —$CH_2CH(OH)CH_2OH$.

The compound of formula (IB) can have $R_4$ be —$CH(C(O)OH)CH_2C(O)OH$.

The compound of formula (IB) can have $R_4$ be —$(CH_2)_2C(O)OCH_2CH(C_2H_5)C_4H_9$.

The compound of formula (IB) can have $R_4$ be —$(CH_2)_2C(O)OH$.

Another aspect of the invention is a method of inhibiting corrosion at a surface. The method comprising contacting the surface with an anti-corrosion composition comprising a compound of formula (II)

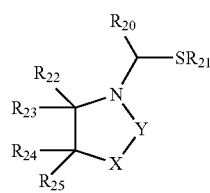

(II)

wherein $R_{20}$ is hydrogen, alkyl, aryl, alkenyl, or heterocyclo; $R_{21}$ is alkyl, aryl, alkenyl, or heterocyclo; $R_{22}$ and $R_{25}$ are independently hydrogen, alkyl, aryl, or together with the carbon atoms they are attached to form a fused ring; $R_{23}$ and $R_{24}$ are hydrogen, combine to form a double bond between the carbon atoms, or when $R_{22}$ and $R_{25}$ form a fused ring, $R_{23}$ and $R_{24}$ form a double bond between the carbon atoms; Y is —$CR_{26}R_{27}$—, —$CR_{26}R_{27}CR_{26}R_{27}$—, —C(O)—, —C(S)—, —$S(O_2)$—; X is —$CR_{28}R_{29}$—, —O—, —S—, —$NR_{30}$—, —$N(C(R_{20})SR_{21})$—; $R_{26}$, $R_{27}$, $R_{28}$, $R_{29}$, and $R_{30}$ are independently hydrogen, alkyl, or aryl.

The anti-corrosion composition can comprise the compound of formula (II).

For the compound of formula (II), $R_{22}$, $R_{23}$, $R_{24}$, and $R_{25}$ are preferably hydrogen, or $R_{22}$ and $R_{25}$ together with the carbon atoms they are attached to form a fused ring and $R_{23}$ and $R_{24}$ combine to form a double bond between the carbon atoms.

For the compound of formula (II), $R_{20}$ can be hydrogen, alkyl, or aryl.

The compound of formula (II) can have $R_{20}$ be hydrogen, methyl, ethyl, propyl, or phenyl.

The compound of formula (II) can have $R_{20}$ be hydrogen, methyl, or phenyl. Preferably, $R_{20}$ can be hydrogen.

For the compound of formula (II), Y can be —$CR_{26}R_{27}$—, or —$CR_{26}R_{27}CR_{26}R_{27}$—.

For the compound of formula (II), X can be —$CR_{28}R_{29}$—, —O—, or —S—.

For the compound of formula (II), preferably, $R_{26}$, $R_{27}$, $R_{28}$, $R_{29}$, and $R_{30}$ are hydrogen.

The compound of formula (II) can have $R_{21}$ be $C_1$-$C_{24}$ alkyl, $C_1$-$C_{24}$ alkenyl, $C_6$-$C_{12}$ aryl, monocyclic or bicyclic heteroaryl, or $C_3$-$C_8$ cycloalkyl, wherein said alkyl, alkenyl, aryl, heteroaryl, or cycloalkyl are each independently unsubstituted or substituted with 1 to 3 substituents independently selected from —F, —Cl, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_{10}$ and $R_{11}$, at each occurrence, are each independently hydrogen or $C_1$-$C_6$ alkyl; or optionally one or more of the —$CH_2$— groups of $R_{21}$ is replaced with a —C(O)O— group.

The compound of formula (II) can have $R_{21}$ be $C_1$-$C_{12}$ alkyl, or $C_1$-$C_{12}$ alkyl substituted with 1 to 3 substituents of —OH or —$CO_2H$; or $R_{21}$ can be $C_1$-$C_{12}$ alkyl wherein one or more of the —$CH_2$— groups is replaced with a —C(O)O— group. Preferably, $R_{21}$ is $C_1$-$C_4$ alkyl, or $C_1$-$C_4$ alkyl substituted with 1 to 3 substituents of —OH or —$CO_2H$; or $R_{21}$ can be $C_1$-$C_4$ alkyl wherein one or more of the —$CH_2$— groups is replaced with a —C(O)O— group.

A further aspect of the invention is a method of inhibiting corrosion at a surface. The method comprising contacting the surface with an anti-corrosion composition comprising a compound of formula (III)

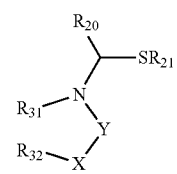

(III)

wherein $R_{20}$ is hydrogen, alkyl, aryl, alkenyl, or heterocyclo; $R_{21}$ is alkyl, aryl, alkenyl, or heterocyclo; Y is —$CR_{26}R_{27}$—, —$CR_{26}R_{27}CR_{26}R_{27}$—, —C(O)—, —C(S)—, —$S(O_2)$—; X is —$CR_{28}R_{29}$—, —O—, —S—, —$NR_{30}$—, —$N(C(R_{20})SR_{21})$—; $R_{26}$, $R_{27}$, $R_{28}$, $R_{29}$, and $R_{30}$ are independently hydrogen, alkyl, or aryl; and $R_{31}$ and $R_{32}$ are alkyl, alkenyl, alkynyl, or aryl.

The anti-corrosion composition can comprise the compound of formula (III).

For the compound of formula (III), $R_{31}$ and $R_{32}$ are preferably alkyl or aryl.

For the compound of formula (III), $R_{20}$ can be hydrogen, alkyl, or aryl.

The compound of formula (III) can have $R_{20}$ be hydrogen, methyl, ethyl, propyl, or phenyl.

The compound of formula (III) can have $R_{20}$ be hydrogen, methyl, or phenyl. Preferably, $R_{20}$ can be hydrogen.

For the compound of formula (III), Y can be —$CR_{26}R_{27}$—, or —$CR_{26}R_{27}CR_{26}R_{27}$—.

For the compound of formula (III), X can be —$CR_{28}R_{29}$—, —O—, or —S—.

For the compound of formula (III), preferably, $R_{26}$, $R_{27}$, $R_{28}$, $R_{29}$, and $R_{30}$ are hydrogen.

The compound of formula (III) can have $R_{21}$ be $C_1$-$C_{24}$ alkyl, $C_1$-$C_{24}$ alkenyl, $C_6$-$C_{12}$ aryl, monocyclic or bicyclic heteroaryl, or $C_3$-$C_8$ cycloalkyl, wherein said alkyl, alkenyl, aryl, heteroaryl, or cycloalkyl are each independently unsubstituted or substituted with 1 to 3 substituents independently selected from —F, —Cl, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_{10}$ and $R_{11}$, at each occurrence, are each independently hydrogen or $C_1$-$C_6$ alkyl; or optionally one or more of the —$CH_2$— groups of $R_{21}$ is replaced with a —C(O)O— group.

The compound of formula (III) can have $R_{21}$ be $C_1$-$C_{12}$ alkyl, or $C_1$-$C_{12}$ alkyl substituted with 1 to 3 substituents of —OH or —$CO_2H$; or $R_{21}$ can be $C_1$-$C_{12}$ alkyl wherein one or more of the —$CH_2$— groups is replaced with a —C(O) O— group. Preferably, $R_{21}$ is $C_1$-$C_4$ alkyl, or $C_1$-$C_4$ alkyl substituted with 1 to 3 substituents of —OH or —$CO_2H$; or $R_{21}$ can be $C_1$-$C_4$ alkyl wherein one or more of the —$CH_2$— groups is replaced with a —C(O)O— group.

A further aspect of the invention is a method of inhibiting corrosion at a surface. The method comprising contacting the surface with an anti-corrosion composition comprising a compound of formula (IV)

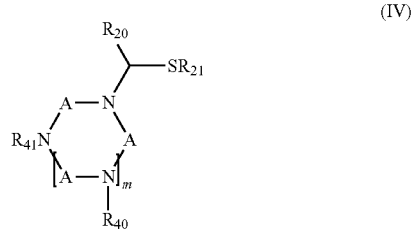

(IV)

wherein $R_{20}$ is hydrogen, alkyl, aryl, alkenyl, or heterocyclo; $R_{21}$ is alkyl, aryl, alkenyl, or heterocyclo; A is —$CR_{26}R_{27}$—, —$(CR_{26}R_{27})_2$—, —$(CR_{26}R_{27})_3$—, —$(CR_{26}R_{27})_4$—; and $R_{40}$ and $R_{41}$ are independently hydrogen, alkyl, or —$C(R_{20})SR_{21}$.

The anti-corrosion composition can comprise the compound of formula (IV).

For the compound of formula (IV), $R_{40}$ and $R_{41}$ are independently hydrogen, or —$C(R_{20})SR_{21}$.

For the compound of formula (IV), $R_{20}$ can be hydrogen, alkyl, or aryl.

The compound of formula (IV) can have $R_{20}$ be hydrogen, methyl, ethyl, propyl, or phenyl.

The compound of formula (IV) can have $R_{20}$ be hydrogen, methyl, or phenyl. Preferably, $R_{20}$ can be hydrogen.

The compound of formula (IV) can have $R_{26}$ and $R_{27}$ be hydrogen.

The compound of formula (IV) can have $R_{21}$ be $C_1$-$C_{24}$ alkyl, $C_1$-$C_{24}$ alkenyl, $C_6$-$C_{12}$ aryl, monocyclic or bicyclic heteroaryl, or $C_3$-$C_8$ cycloalkyl, wherein said alkyl, alkenyl, aryl, heteroaryl, or cycloalkyl are each independently unsubstituted or substituted with 1 to 3 substituents independently selected from —F, —Cl, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_{10}$ and $R_{11}$, at each occurrence, are each independently hydrogen or $C_1$-$C_6$ alkyl; or optionally one or more of the —$CH_2$— groups of $R_{21}$ is replaced with a —C(O)O— group.

The compound of formula (IV) can have $R_{21}$ be $C_1$-$C_{12}$ alkyl, or $C_1$-$C_{12}$ alkyl substituted with 1 to 3 substituents of —OH or —$CO_2H$; or $R_{21}$ can be $C_1$-$C_{12}$ alkyl wherein one or more of the —$CH_2$— groups is replaced with a —C(O)O— group. Preferably, $R_{21}$ is $C_1$-$C_4$ alkyl, or $C_1$-$C_4$ alkyl substituted with 1 to 3 substituents of —OH or —$CO_2H$; or $R_{21}$ can be $C_1$-$C_4$ alkyl wherein one or more of the —$CH_2$— groups is replaced with a —C(O)O— group.

The anti-corrosion composition can further comprise one or more additional components, including but not limited to, additional corrosion inhibitors, solvents, asphaltene inhibitors, paraffin inhibitors, scale inhibitors, emulsifiers, water clarifiers, dispersants, emulsion breakers, gas hydrate inhibitors, biocides, pH modifiers, or surfactants.

The surface can be a part of equipment used in the production, transportation, storage, and/or separation of crude oil or natural gas.

More specifically, the surface can be a part of equipment used a coal-fired process, a waste-water process, a farm, a slaughter house, a land-fill, a municipality waste-water plant, a coking coal process, or a biofuel process. Preferably, the surface can be a part of equipment used in the production of crude oil or natural gas.

The anti-corrosion composition can comprise from about 0.1 to about 20 wt. % of one or more compounds of formula (I) in a 1:1 water:glycol ether solvent system.

The anti-corrosion compositions can partially or completely suppress the production of hydrogen sulfide upon storage of the compositions. Thus, the anti-corrosion compositions have an undetectable amount of hydrogen sulfide upon storage for at least 30 days at a temperature of 25° C.

The compounds of formula 1 can be prepared by reacting an appropriate thiol compound with one or more equivalents of formaldehyde (or formalin or paraformaldehyde):

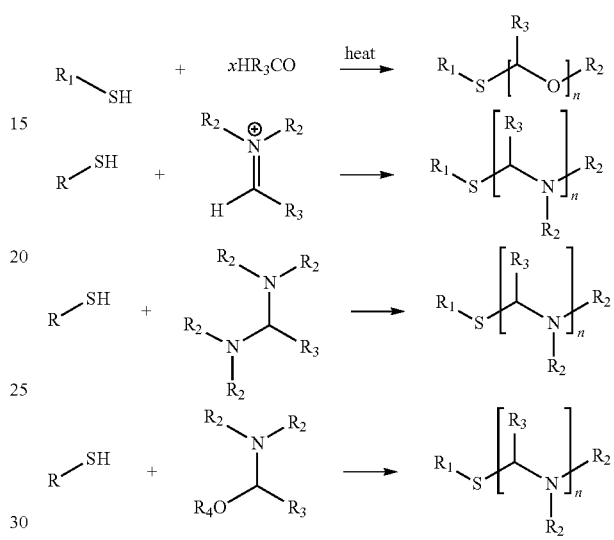

wherein $R_1$ is alkyl, aryl, alkenyl, heterocyclo, or $R_1$ and $R_2$ together with the sulfur, carbon, and oxygen atoms form a ring; n is an integer from 1 to 10; $R_2$ is hydrogen, or $R_1$ and $R_2$ together with the sulfur, carbon, and oxygen atoms form a ring: and $R_3$ is hydrogen, alkyl, alkaryl, aryl, or heterocyclo. When $R_2$ is alkyl, alkenyl, aryl, another reaction occurs between the hydroxy group and the appropriate reagent.

Suitable additional corrosion inhibitors for inclusion in the compositions include, but are not limited to, alkyl, hydroxyalkyl, alkylaryl, arylalkyl or arylamine quaternary salts; mono or polycyclic aromatic amine salts; imidazoline derivatives; mono-, di- or trialkyl or alkylaryl phosphate esters; phosphate esters of hydroxylamines; phosphate esters of polyols; and monomeric or oligomeric fatty acids.

Suitable alkyl, hydroxyalkyl, alkylaryl arylalkyl or arylamine quaternary salts include those alkylaryl, arylalkyl and arylamine quaternary salts of the formula $[N^+R^{5a}R^{6a}R^{7a}R^{8a}][X^-]$, wherein $R^{5a}$, $R^{6a}$, $R^{7a}$, and $R^{8a}$ contain one to 18 carbon atoms, and X is Cl, Br or I. Further, $R^{5a}$, $R^{6a}$, $R^{7a}$, and $R^{8a}$ are each independently alkyl (e.g., $C_1$-$C_{18}$ alkyl), hydroxyalkyl (e.g., $C_1$-$C_{18}$ hydroxyalkyl), or arylalkyl (e.g., benzyl). The mono or polycyclic aromatic amine salt with an alkyl or alkylaryl halide include salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I.

Suitable quaternary ammonium salts include, but are not limited to, tetramethyl ammonium chloride, tetraethyl ammonium chloride, tetrapropyl ammonium chloride, tetrabutyl ammonium chloride, tetrahexyl ammonium chloride, tetraoctyl ammonium chloride, benzyltrimethyl ammonium chloride, benzyltriethyl ammonium chloride, phenyltrimethyl ammonium chloride, phenyltriethyl ammonium chloride, cetyl benzyldimethyl ammonium chloride, hexadecyl trimethyl ammonium chloride, dimethyl alkyl benzyl quaternary ammonium compounds, monomethyl dialkyl benzyl quaternary ammonium compounds, trimethyl benzyl quaternary ammonium compounds, and trialkyl benzyl quaternary ammonium compounds, wherein the alkyl group can contain between about 6 and about 24 carbon atoms, about 10 and about 18 carbon atoms, or about 12 to about 16 carbon atoms. Suitable quaternary ammonium compounds (quats) include, but are not limited to, trialkyl, dialkyl, dialkoxy alkyl, monoalkoxy, benzyl, and imidazolinium quaternary ammonium compounds, salts thereof, the like, and combinations thereof. The quaternary ammonium salt can be an alkylamine benzyl quaternary ammonium salt, a benzyl triethanolamine quaternary ammonium salt, or a benzyl dimethylaminoethanolamine quaternary ammonium salt.

The additional corrosion inhibitor can be a quaternary ammonium or alkyl pyridinium quaternary salt such as those represented by the general formula:

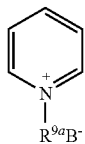

wherein $R^{9a}$ is an alkyl group, an aryl group, or an arylalkyl group, wherein said alkyl groups have from 1 to about 18 carbon atoms and B is Cl, Br or I. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium and an alkyl benzyl pyridinium chloride, preferably wherein the alkyl is a $C_1$-$C_6$ hydrocarbyl group. The corrosion inhibitor can include benzyl pyridinium chloride.

The additional corrosion inhibitor can be an imidazoline derived from a diamine, such as ethylene diamine (EDA), diethylene triamine (DETA), triethylene tetraamine (TETA) etc. and a long chain fatty acid such as tall oil fatty acid (TOFA). Suitable imidazolines include those of formula:

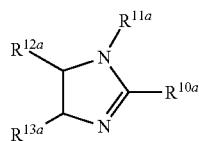

wherein $R^{12a}$ and $R^{13a}$ are independently a $C_1$-$C_6$ alkyl group or hydrogen, $R^{11a}$ is hydrogen, $C_1$-$C_6$ alkyl, $C_1$-$C_6$ hydroxyalkyl, or $C_1$-$C_6$ arylalkyl, and $R^{10a}$ is a $C_1$-$C_{20}$ alkyl or a $C_1$-$C_{20}$ alkoxyalkyl group. For the imidazolines, $R^{11a}$, $R^{12a}$ and $R^{13a}$ are each hydrogen and $R^{10a}$ is the alkyl mixture typical in tall oil fatty acid (TOFA).

The additional corrosion inhibitor compound can be an imidazolinium compound of the following formula:

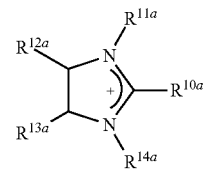

wherein $R^{12a}$ and $R^{13a}$ are independently a $C_1$-$C_6$ alkyl group or hydrogen, $R^{11a}$ and $R^{14a}$ are independently hydrogen, $C_1$-$C_6$ alkyl, $C_1$-$C_6$ hydroxyalkyl, or $C_1$-$C_6$ arylalkyl, and $R^{10}$ is a $C_1$-$C_{20}$ alkyl or a $C_1$-$C_{20}$ alkoxyalkyl group.

Suitable mono-, di- and trialkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethyl phosphate with triethylphosphate producing a more broad distribution of alkyl phosphate esters. Alternatively, the phosphate ester may be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor compound can further be a monomeric or oligomeric fatty acid. Preferred are $C_{14}$-$C_{22}$ saturated and unsaturated fatty acids as well as dimer, trimer and oligomer products obtained by polymerizing one or more of such fatty acids.

An anticorrosion composition of the invention can comprise from 0 to 80 percent, 0 to 60 percent, or 0 to 50 percent by weight of one or more additional corrosion inhibitors, based on total weight of the composition. A composition of the invention can comprise from 0 to 10 percent by weight of one or more additional corrosion inhibitors, based on total weight of the composition. A composition of the invention can comprise 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt %, 13.5 wt %, 14.0 wt %, 14.5 wt %, or 15.0 wt % by weight of one or more additional corrosion inhibitors, based on total weight of the composition. Each system can have its own requirements, and the weight percent of one or more additional corrosion inhibitors in the composition can vary with the system in which it is used.

The compositions disclosed herein can include a solvent. The solvent can be present in an amount of 5 wt. % to about 95 wt. %, about 20 wt. % to about 80 wt. %, or about 40 wt. % to about 60 wt. %, based on total weight of the composition. The solvent can constitute about 5, 10, 15, 20, 25, 30, 35, 40, 45, 50, 55, 60, 65, 70, 75, 80, 85, 90 or 95 wt. % of the composition.

Suitable solvents include, but are not limited to, alcohols, hydrocarbons, ketones, ethers, alkylene glycols, glycol ethers, amides, nitriles, sulfoxides, esters, and water. The solvent can be water, isopropanol, methanol, ethanol, 2-ethylhexanol, heavy aromatic naphtha, toluene, ethylene glycol, ethylene glycol monobutyl ether (EGMBE), diethylene glycol monoethyl ether, or xylene. Representative polar solvents suitable for formulation with the composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), alkylene glycols (methylene glycol, ethylene glycol, 1,2-propylene glycol, 1,3-propylene glycol, etc.) glycol ethers (diethyleneglycol monomethyl ether, ethylene glycol monobutyl ether, ethylene glycol dibutyl ether, etc.), ketones (cyclohexanone, diisobutylketone), ethers (diethyl ether, etc.), an alkylene carbonate (propylene carbonate, etc.), N-methylpyrrolidinone (NMP), N,N-dimethylformamide, a polyol (glycerin, etc.), and the like. Representative non-polar solvents suitable for formulation with the composition include aliphatic hydrocarbons such as pentane, hexane, cyclohexane, methylcyclohexane, heptane, decane, dodecane, diesel, and the like; aromatic hydrocarbons such as toluene, xylene, heavy aromatic naphtha; and fatty acid derivatives (acids, esters, amides), and the like.

The solvent can be a solvent compatible with an arctic environment, as for example, methanol, ethanol, ethylene glycol or glycerin, which improves the anti-freeze properties of the composition. Such solvent is typically present in an amount of about 5 to about 15 wt. %, and preferably about 10 wt. %, based on total weight of the composition to have an anti-freeze effect.

The anticorrosion composition can further comprise an organic sulfur compound, such as a mercaptoalkyl alcohol, mercaptoacetic acid, thioglycolic acid, 3,3'-dithiodipropionic acid, thiosulfate, thiourea, L-cysteine, or tert-butyl mercaptan. Preferably, the mercaptoalkyl alcohol comprises 2-mercaptoethanol. The organic sulfur compound can constitute 0 to 15 wt. % of the composition, based on total weight of the composition, preferably about 1 to about 10 wt. % and more preferably about 1 to about 5 wt. %. The solvent stabilizer can constitute 1, 2, 3, 4, 5, 6, 7, 8, 9, 10, 11, 12, 13, 14 or 15 wt. % of the composition.

The anticorrosion composition can further include a demulsifier. Preferably, the demulsifier comprises an oxyalkylate polymer, such as a polyalkylene glycol. The demulsifier can constitute 0.5 to 5 wt. % of the composition, based on total weight of the composition. The demulsifier can constitute 0.5, 1, 1.5, 2, 2.5, 3, 3.5, 4, 4.5 or 5 wt. % of the composition.

The anticorrosion compositions can optionally include one or more other additives. Suitable additives include, but are not limited to, asphaltene inhibitors, paraffin inhibitors, scale inhibitors, emulsifiers, water clarifiers, dispersants, emulsion breakers, hydrogen sulfide scavengers, gas hydrate inhibitors, biocides, pH modifiers, or surfactants.

The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The composition can comprise from about 0.1 to 10 wt. %, from about 0.1 to 5 wt. %, or from about 0.5 to 4 wt. % of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable dispersants include, but are not limited to, dodecyl benzene sulfonate, oxyalkylated alkylphenols, and oxyalkylated alkylphenolic resins.

The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

The composition can comprise from about 0.5 to 20 wt. %, from about 1 to 15 wt. %, or from about 1 to 10 wt. % of an additional hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The composition can comprise from about 0.1 to 25 wt. %, from about 0.5 to 20 wt. %, or from about 1 to 10 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The composition can comprise from about 0.1 to 25 wt. %, from about 0.5 to 20 wt. %, or from about 1 to 10 wt. % of a kinetic hydrate inhibitor or anti-agglomerate, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

The surfactant can be a quaternary ammonium compound, an amine oxide, an ionic or nonionic surfactant, or any combination thereof. Suitable quaternary amine compounds include, but are not limited to, alkyl benzyl ammonium chloride, benzyl cocoalkyl($C_{12}$-$C_{18}$)dimethylammonium chloride, dicocoalkyl ($C_{12}$-$C_{18}$)dimethylammonium chloride, ditallow dimethylammonium chloride, di(hydrogenated tallow alkyl)dimethyl quaternary ammonium methyl chloride, methyl bis(2-hydroxyethyl cocoalkyl($C_{12}$-$C_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, and hydrogenated tallow alkyl (2-ethylhexyl) dimethyl quaternary ammonium methyl sulfate.

Corrosion inhibitor compositions made according to the invention can further include additional functional agents or additives that provide a beneficial property. For example, additional agents or additives can comprise pH adjusters or other neutralizing agents, surfactants, emulsifiers, sequestrants, solubilizers, other lubricants, buffers, detergents, cleaning agent, rinse aid composition, secondary anti-corrosion agent, preservatives, binders, thickeners or other viscosity modifiers, processing aids, carriers, water-conditioning agents, foam inhibitors or foam generators, threshold agent or system, aesthetic enhancing agent (i.e., dye, odorant, perfume), other agents or additives suitable for formulation with a corrosion inhibitor composition and the like, and mixtures thereof. Additional agents or additives will vary according to the particular corrosion inhibitor composition being manufactured and its intend use.

Alternatively, the compositions may not contain any of the additional agents or additives and can be comprised of the compound of formula (I), (II), (III) or (IV).

The compositions of the invention can be used for inhibiting corrosion in oil and gas applications.

The compositions can be used for inhibiting corrosion by treating a gas or liquid stream with an effective amount of a compound or composition of the invention, as described herein.

The compositions of the invention can be used in any industry where it is desirable to inhibit corrosion at a surface.

The compositions can be used in water systems, condensate/oil systems/gas systems, or any combination thereof. The compositions can be applied to a gas or liquid produced or used in the production, transportation, storage, and/or separation of crude oil or natural gas. The compositions can be applied to a gas stream used or produced in a coal-fired process, such as a coal-fired power plant. The compositions can be applied to a gas or liquid produced or used in a waste-water process, a farm, a slaughter house, a land-fill, a municipality waste-water plant, a coking coal process, or a biofuel process.

A fluid to which the compositions can be introduced can be an aqueous medium. The aqueous medium can comprise water, gas, and optionally liquid hydrocarbon. A fluid to which the compositions can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid or gas can be a refined hydrocarbon product.

A fluid or gas treated with a composition of the invention can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C. The fluid or gas can be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. The fluid or gas can be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The compositions of the invention can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the compositions of the invention are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units. The fluid or gas can be contained in water systems, condensate/oil systems/gas systems, or any combination thereof.

The compositions of the invention can be introduced into a fluid or gas by any appropriate method for ensuring dispersal through the fluid or gas. The inhibitor composition is added at a point in a flow line upstream from the point at which corrosion prevention is desired. The compositions can be injected using mechanical equipment such as chemical injection pumps, piping tees, injection fittings, atomizers, quills, and the like. The compositions of the invention can be introduced with or without one or more additional polar or non-polar solvents depending upon the application and requirements. The compositions of the invention can be pumped into an oil and/or gas pipeline using an umbilical line. Capillary injection systems can be used to deliver the compositions to a selected fluid. The compositions can be introduced into a liquid and mixed. The compositions can be injected into a gas stream as an aqueous or nonaqueous solution, mixture, or slurry. The fluid or gas can be passed through an absorption tower comprising a compound or composition of the invention.

The compositions can be applied to a fluid or gas to provide any selected concentration. In practice, the compositions of the invention are typically added to a flow line to provide an effective treating dose of actives (i.e., the described compound(s) or composition(s)) from about 0.01 to about 5,000 ppm. The compositions can be applied to a fluid or gas to provide an actives concentration of about 1 parts per million (ppm) to about 1,000,000 ppm, about 1 parts per million (ppm) to about 100,000 ppm, or about 10 ppm to about 75,000 ppm. The compositions can be applied to a fluid to provide an actives concentration of about 100 ppm to about 10,000 ppm, about 200 ppm to about 8,000 ppm, or about 500 ppm to about 6,000 ppm.

The compositions can be applied to a fluid or gas to provide an actives concentration of 0.1 ppm, 0.5 ppm, 1 ppm, 2 ppm, 5 ppm, 10 ppm, 20 ppm, 100 ppm, 200 ppm, 500 ppm, or 1,000 ppm. The compositions can be applied to a fluid or gas to provide an actives concentration of 0.125 ppm, 0.25 ppm, 0.625 ppm, 1 ppm, 1.25 ppm, 2.5 ppm, 5 ppm, 10 ppm, or 20 ppm. Each system can have its own dose level requirements, and the effective dose level of a composition to sufficiently reduce the rate of corrosion can vary with the system in which it is used.

The compositions can be applied continuously, in batch, or a combination thereof. The composition doses can be continuous to prevent corrosion. The composition doses can be intermittent (i.e., batch treatment) or the composition doses can be continuous/maintained and/or intermittent to inhibit corrosion.

Dosage rates for continuous treatments typically range from about 10 to about 500 ppm, or about 10 to about 200 ppm. Dosage rates for batch treatments typically range from about 10 to about 400,000 ppm, or about 10 to about 20,000 ppm. The composition can be applied as a pill to a pipeline, providing a high dose (e.g., 20,000 ppm) of the composition.

The flow rate of a flow line in which the composition is used can be between 0 and 100 feet per second, or between 0.1 and 50 feet per second. The compositions can also be formulated with water in order to facilitate addition to the flow line.

The compositions can provide at least 80, 81, 82, 83, 84, 85, 86, 87, 88, 89, 90, 91, 92, 93, 94, 95, 96, 97, 98, or 99% corrosion protection for a solid, optionally as defined by a 1018 carbon steel coupon in a wheel box test. A wheel box test can be performed according to NACE publication ID182 (December 1982). The wheel box is a test that is often used to compare the performance of one corrosion inhibitor to another. A composition of the invention can provide at least 80%, at least 85%, or at least 90% corrosion protection for a 1018 carbon steel coupon in a wheel box test, wherein the wheel box test is characterized by a testing temperature of about 176° F.; a $CO_2$ saturated liquid medium of 10% LVT-200 oil and 90% ASTM Seawater brine; a test duration of 24 hours; and an inhibitor dosage of 20 ppm based on total fluids. A composition of the invention provides 80%, 81%, 82%, 83%, 84%, 85%, 86%, 87%, 88%, 89%, 90%, 91%, 92%, 93%, 94%, 95%, 96%, 97%, 98%, or 99% A corrosion protection for a 1018 carbon steel coupon in a wheel box test, wherein the wheel box test is characterized by a testing temperature of about 176° F.; a $CO_2$ saturated liquid medium of 10% LVT-200 oil and 90% ASTM Seawater brine; a test duration of 24 hours; and an inhibitor dosage of 20 ppm based on total fluids.

The compositions can evolve 250 ppm or less, 200 ppm or less, 150 ppm or less, 100 ppm or less, 50 ppm or less, 30 ppm or less, 25 ppm or less, 20 ppm or less, 15 ppm or less, 10 ppm or less, 9 ppm or less, 8 ppm or less, 7 ppm or less, 6 ppm or less, 5 ppm or less, 4 ppm or less, 3 ppm or less, 2 ppm or less, 1 ppm or less, or 0 ppm of sulfur species into a headspace. The headspace sulfur species concentration can be determined by placing a sample of the composition (e.g., 40 g) into a sealed receptacle (e.g., an 8 ounce glass jar sealed with a cap containing a hole fitted with a rubber stopper which is used for sampling); aging the composition at a selected temperature for a selected time period (e.g., in a 50° C. oven over a period of 10 days); and sampling the headspace for sulfur species (e.g., with detection tubes, such as GasTec sulfur detection tubes). The sulfur species quantified can include hydrogen sulfide, mercaptans (e.g., methyl mercaptan, ethyl mercaptan, and the like), sulfur dioxide, and/or carbonyl sulfide.

The compositions of the invention can be used for inhibiting corrosion in other applications.

The compositions are useful for corrosion inhibition of containers, processing facilities, or equipment in the food service or food processing industries. The compositions have particular value for use on food packaging materials and equipment, and especially for cold or hot aseptic packaging. Examples of process facilities in which the compositions can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The compositions can be used to inhibit corrosion in tanks, lines, pumps, and other equipment used for the manufacture and storage of soft drink materials, and also used in the bottling or containers for the beverages.

The compositions can also be used on or in other industrial equipment and in other industrial process streams such as heaters, cooling towers, boilers, retort waters, rinse waters, aseptic packaging wash waters, and the like. The compositions can be used to treat surfaces in recreational waters such as in pools, spas, recreational flumes and water slides, fountains, and the like.

The compositions can be used to inhibit the corrosion of metal surfaces contacted with cleaners in surfaces found in janitorial and/or housekeeping applications, food processing equipment and/or plant applications, and in laundry applications. For example, the corrosion of washers, such as tunnel washers for washing textiles, can be inhibited according to methods disclosed herein.

The compositions can be used or applied in combination with low temperature dish and/or warewash sanitizing final rinse, toilet bowl cleaners, and laundry bleaches. The compositions and methods can be used to treat metal surfaces, such as ware, cleaned and/or sanitized with corrosive sources.

The compositions and methods disclosed herein protect surfaces from corrosion caused by hypochlorite bleach. A method can include providing the corrosion inhibitor composition to a surface treated with a hypochlorite solution in order to inhibit corrosion caused by the hypochlorite solution. The method can include preparing an aqueous use composition of the present corrosion inhibitor composition. The method can further include contacting a surface, such as a hard metal surface, in need of corrosion inhibition due to contact with a hypochlorite solution.

The corrosion inhibitor compositions can be dispensed in any suitable method generally known by one skilled in the art. For example, a spray-type dispenser can be used, such as that disclosed in U.S. Pat. Nos. 4,826,661, 4,690,305, 4,687,121, 4,426,362 and in U.S. Pat. Nos. Re 32,763 and 32,818, the disclosures of which are incorporated by reference herein. A spray-type dispenser functions by impinging a water spray upon an exposed surface of a composition to dissolve a portion of the composition, and then immediately directing the concentrate solution including the composition out of the dispenser to a storage reservoir or directly to a point of use.

The compositions can be dispensed by immersing either intermittently or continuously in water. The composition can then dissolve, for example, at a controlled or predetermined rate. The rate can be effective to maintain a concentration of dissolved agent that is effective for use according to the methods disclosed herein.

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle" or "heterocyclyl," as used herein, refers to a monocyclic, bicyclic, or tricyclic group containing 1 to 4 heteroatoms selected from N, O, S(O)$_n$, P(O)$_n$, PR$_z$, NH or NR$_z$, wherein R$_z$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy," as used herein, refers to an —OH group.

The term "sweetening," as used herein, may refer to a process that removes sulfur species from a gas or liquid. The sulfur species may include hydrogen sulfide and mercaptans.

The term "sour gas," as used herein, may refer to a gas that includes significant amounts of sulfur species, such as hydrogen sulfide and/or mercaptans.

The term "sour liquid" or "sour fluid," as used herein, may refer to a liquid that includes significant amounts of sulfur species, such as hydrogen sulfide and/or mercaptans.

The term "water cut," as used herein, means the percentage of water in a composition containing an oil and water mixture.

Having described the invention in detail, it will be apparent that modifications and variations are possible without departing from the scope of the invention defined in the appended claims.

EXAMPLES

The following non-limiting examples are provided to further illustrate the invention.

Example 1: Reaction of Mercaptoethanol with Paraformaldehyde

Under normal atmospheric conditions, 2-mercaptoethanol (1 mol) is added to solid paraformaldehyde (1 mol) and catalytic triethanolamine (0.0064 mol) charged to a suitable volume round bottom flask equipped with a reflux condenser and a magnetic stir bar. The slurry was heated to 80° C. under stirring for 4 h at which time the mixture became homogeneous. In some instances an amine is added to the solution and allowed to react for an additional 2 hours. The solution was allowed to cool to ambient temperature before submitting for NMR analysis to determine the extent of reaction.

Example 2: Wheel Box Tests

Table 1 details exemplary sulfide formyl derivatives of Formula (IA) that can be prepared by the method of Example 1 and used as corrosion inhibitors

TABLE 1

Examples of thio-hemiformyl products
Thiol-hemiformyl examples

| Reference Cpd. | Thiol component | Aldehyde |
|---|---|---|
| TGA (comparative) | thioglycolic acid | N/A |
| 2ME (comparative) | 2-mercaptoethanol | N/A |
| Ex. A | 2-mercaptoethanol | formaldehyde |
| Ex. B | 2-mercaptoethanol | formaldehyde (1.5 eq.) |
| Ex. C | 2-mercaptoethanol | formaldehyde (2 eq.) |
| Ex. D | 2-mercaptoethanol | formaldehyde (3 eq.) |
| Ex. E | 2-mercaptoethanol | formaldehyde (4 eq.) |
| Ex. F | cyclohexyl thiol | formaldehyde |
| Ex. G | Mercaptohexanol | formaldehyde |

TABLE 1-continued

Examples of thio-hemiformyl products
Thiol-hemiformyl examples

| Reference Cpd. | Thiol component | Aldehyde |
|---|---|---|
| Ex. H | isopropyl thiol | formaldehyde |
| Ex. I | Dodecylthiol | formaldehyde |
| Ex. J | Thioglycerol | formaldehyde |
| Ex. K | mercaptosuccinnic acid | formaldehyde |
| Ex. L | 2-ethylhexyl mercaptopropioate | formaldehyde |
| Ex. M | mercaptopropionic acid | formaldehyde |
| Ex. N | 2-mercaptoethanol | formaldehyde (0.95 eq.) |
| Ex. O | 2-mercaptoethanol | formaldehyde (0.90 eq.) |
| Ex. P | 2-mercaptoethanol | formaldehyde (0.75 eq.) |
| Ex. Q | 2-mercaptoethanol | formaldehyde (0.50 eq.) |

To illustrate the corrosion inhibiting ability of compounds and compositions of the invention, corrosion inhibitor solutions were prepared by dissolving the sulfide formyl derivative of interest to 2.5 wt. % in a suitable solvent. Since it is known that thiol-containing compounds readily improve the corrosion inhibiting properties of other traditional corrosion inhibitor molecules, a second set of formulations were prepared to illustrate this effect. To this end, additional formulations were prepared by dissolving a 2.5 wt % solution of sulfide formyl derivative with 7.5 wt % solutions of quaternary amine based corrosion inhibitors in a suitable solvent. The performance of these two sets of corrosion inhibitor formulations were subsequently tested for performance using a wheel box test method, the results of which are shown in Tables 2 and 3.

Wheel box tests are typically used as a screening method for assessing the corrosion inhibiting ability of additives to a corrosive solution. Compounds of the invention were tested for the ability to act as corrosion inhibitors alone and in combination with other known corrosion inhibitor actives, specifically quaternary ammonium salt compounds.

The following sets of conditions were used to compare the corrosion inhibiting ability of a variety of sulfide formyl derivatives in wheel box testing:

Temperature: 80° C. (176° F.)
Oil: LVT-200 (kerosene)
Brine: Synthetic seawater brine
Water cut: 90%
$pCO_2$: atmospheric pressure
Duration: 24 hours
Metal Coupon: C1018 Mild Steel Wheel box tests were performed in accordance with NACE standard methods. Briefly, pre-weighed and measured metal coupons are added to the test fluids in a sealed vessel which is constantly rotated under the conditions described above. Corrosion rates are calculated by measuring the amount of metal loss (weight) throughout the duration of the test and by the surface area of metal available. Corrosion rates are compared between uninhibited and inhibited solutions in order to calculate a % protection of specific formulations. Corrosion inhibitor performance was compared to that of an untreated blank sample as well as a range of dose rates to show performance with respect to concentration. All data is reported as a corrosion rate in mils per year (mpy). The data shown in Table 2 clearly demonstrates the effectiveness of compounds of the invention toward reducing the corrosion rate of the fluids.

A number of sulfide formyl derivatives were compared to that of an organic thiol, namely 2-mercaptoethanol, commonly used for corrosion protection of internal oilfield production equipment from both $CO_2$ and $H_2S$ acid corrosion.

TABLE 2

Wheel Box Corrosion Performance Data (mpy) of Thio-hemiformyls

| Reference Cpd. | Thiol-formyl Concentration (ppm) | | | | | % Prot. @ 25 ppm |
|---|---|---|---|---|---|---|
| | 0.5 | 2.5 | 5 | 12.5 | 25 | |
| TGA (comparative) | 36.69 | 27.48 | 26.14 | 24.89 | 25.77 | 61% |
| 2ME (comparative) | 40.75 | 31.96 | 26.44 | 24.43 | 25.68 | 61% |
| Ex. A | 42.30 | 28.85 | 26.08 | 26.32 | 26.41 | 60% |
| Ex. B | 39.25 | 28.00 | 30.50 | 26.20 | 24.95 | 62% |
| Ex. C | 49.35 | 30.99 | 26.41 | 25.19 | 24.61 | 62% |
| Ex. D | 43.22 | 27.08 | 25.38 | 24.86 | 25.59 | 61% |
| Ex. E | 41.11 | 30.84 | 25.96 | 24.92 | 24.43 | 63% |
| Ex. F | 41.45 | 36.84 | 36.51 | 32.45 | 33.06 | 50% |
| Ex. G | 45.72 | 46.51 | 24.22 | 24.00 | 14.55 | 78% |
| Ex. H | 40.14 | 28.40 | 25.86 | 26.29 | 19.83 | 70% |
| Ex. I | 62.22 | 61.24 | 60.57 | 50.11 | 46.12 | 30% |
| Ex. J | 40.26 | 25.22 | 21.69 | 22.02 | 20.95 | 68% |
| Ex. K | 37.00 | 30.10 | 28.88 | 32.18 | 24.89 | 62% |
| Ex. L | 62.53 | 61.55 | 38.31 | 33.34 | 32.18 | 51% |
| Ex. M | 40.14 | 40.26 | 30.56 | 24.58 | 25.56 | 61% |
| Ex. N | 33.46 | 31.57 | 29.98 | 27.60 | 24.13 | 68% |
| Ex. O | 64.14 | 31.32 | 31.23 | 27.82 | 27.45 | 63% |
| Ex. P | 75.82 | 31.87 | 29.25 | 26.78 | 26.90 | 64% |
| Ex. Q | 71.34 | 30.38 | 28.00 | 27.51 | 26.23 | 65% |

A second set of tests were performed under identical conditions as those described above. In a non-limiting example, sulfide formyl derivative type compound were used in combination with an organic quaternary ammonium salt in order to illustrate the advantageous properties between organic thio-formyl compounds and other commonly used organic corrosion inhibitors. The results of these tests can be seen in Table 3 below and are represented as a concentration of sulfur compound in order to show a direct comparison to the data in Table 2.

TABLE 3

Wheel Box Corrosion Performance Data (mpy) of Thio-hemiformyls and quat.

| Reference Cpd. | Thiol-formyl Concentration (ppm) | | | | | % Prot. @ 2.5 ppm |
|---|---|---|---|---|---|---|
| | 0.125 | 0.25 | 0.625 | 1.25 | 2.5 | |
| TGA (comparative) | 23.21 | 12.20 | 4.79 | 2.96 | 2.56 | 96% |
| 2ME (comparative) | 41.91 | 38.19 | 8.39 | 7.87 | 3.05 | 95% |
| Ex. A | 38.13 | 19.61 | 3.54 | 3.36 | 3.45 | 95% |
| Ex. B | 35.72 | 20.59 | 5.37 | 4.27 | 4.30 | 93% |
| Ex. C | 41.30 | 24.64 | 3.45 | 3.26 | 3.75 | 94% |
| Ex. D | 36.02 | 29.49 | 8.85 | 4.18 | 3.93 | 94% |
| Ex. E | 43.89 | 20.59 | 5.40 | 3.39 | 3.54 | 94% |
| Ex. F | 38.49 | 38.86 | 28.58 | 18.42 | 2.47 | 96% |
| Ex. G | 31.11 | 28.94 | 7.32 | 3.45 | 3.66 | 94% |
| Ex. H | 37.03 | 36.20 | 18.97 | 4.61 | 3.72 | 94% |
| Ex. I | 41.85 | 45.05 | 45.57 | 44.35 | 3.81 | 94% |
| Ex. J | 34.10 | 30.01 | 6.77 | 3.05 | 3.05 | 95% |
| Ex. K | 34.92 | 27.27 | 14.64 | 2.87 | 2.78 | 96% |
| Ex. L | 48.50 | 49.44 | 45.20 | 12.26 | 3.81 | 94% |
| Ex. M | 43.49 | 36.75 | 23.03 | 4.33 | 2.96 | 95% |
| Ex. N | 8.72 | 4.71 | 4.12 | 3.90 | 2.68 | 96% |
| Ex. O | 18.33 | 11.13 | 5.28 | 2.93 | 2.10 | 97% |
| Ex. P | 67.98 | 6.28 | 4.54 | 3.11 | 2.20 | 97% |
| Ex. Q | 37.24 | 7.05 | 4.27 | 3.48 | 2.84 | 96% |
| Control | 48.10 | 48.77 | 55.69 | 52.86 | 54.35 | 13% |

Example 3: Headspace Tests

In order to illustrate the added benefit of sulfide formyl derivatives of improving the evolution of volatile sulfur containing degradation components, headspace measurements were performed on example corrosion inhibitor formulations. The headspace measurements were performed in accordance with the standard ASTM-D 5705 method. Briefly, the method used for this screening is to place 40 g of the formulated corrosion inhibitor into an 8 ounce glass jar sealed with a cap containing a hole fitted with a rubber stopper which is used for sampling. The samples were subsequently aged in a 50° C. oven over a period of 7 days before sampling. Samples were analyzed by removal of the rubber stopper and the headspace was subsequently sampled using GasTec sulfur detection tubes.

Two sets of test were performed with samples formulated in different solvents. In one example, a sulfide formyl derivative was dissolved at 5% wt. in heavy aromatic naphtha (identified hereinafter as HAN). In a second example, a sulfide formyl derivative was dissolved at 5% wt. in ethylene glycol monobutyl ether (identified hereinafter as EGMBE) for headspace experiments.

The results of headspace evaluation experiments are shown in Table 4.

TABLE 4

Headspace Results

| Reference | Thiol-formyl | Solvent | Headspace Evaluation (ppm) |
|---|---|---|---|
| Cyclohexyl thiol (Comp.) | N/A | EGMBE | 65 |
| isopropyl thiol (Comp.) | N/A | EGMBE | 20 |
| Ex. A | mercaptoethanol | HAN | 0 |
| Ex. A | mercaptoethanol | EGMBE | 0 |
| Ex. F | cyclohexyl thiol formyl | EGMBE | 0 |
| Ex. G | mercaptohexanol | HAN | 0 |
| Ex. G | mercaptohexanol | EGMBE | 0 |
| Ex. H | isopropyl thiol | EGMBE | 0 |
| Ex. I | dodecylthiol | HAN | 0 |
| Ex. I | dodecylthiol | EGMBE | 0 |
| Ex. J | thioglycerol | HAN | 0 |
| Ex. J | thioglycerol | EGMBE | 0 |
| Ex. K | mercaptosuccinnic acid | EGMBE | 0 |
| Ex. L | 2-ethylhexyl mercaptopropioate | EGMBE | 0 |
| Ex. L | 2-ethylhexyl mercaptopropioate | HAN | 0 |

Example 4

Table 5 details exemplary sulfide formyl derivatives that can be prepared by the method of Example 1, except that the amine is used in stoichiometric amounts to react with the thiol and aldehyde components to form the reaction product. The reaction products are used as corrosion inhibitors.

TABLE 5

Examples of amino-thio-hemiformyls

| Reference Cpd. | Thiol component | Aldehyde | Amine |
|---|---|---|---|
| Ex. R | 2-mercaptoethanol | formaldehyde | Diethanolamine |
| Ex. S | 2-mercaptoethanol | formaldehyde | Morpholine |
| Ex. T | 2-mercaptoethanol | formaldehyde | Diethyl amine |
| Ex. U | 2-mercaptoethanol | formaldehyde | Monoethanolamine |
| Ex. V | 2-mercaptoethanol | formaldehyde | Diethylenetriamine |
| Ex. W | 2-mercaptoethanol | acetaldehyde | None |
| Ex. X | 2-mercaptoethanol | acetaldehyde | Diethanolamine |

To illustrate the corrosion inhibiting ability of compounds and compositions of the invention, corrosion inhibitor solutions were prepared by dissolving the sulfide formyl derivative of interest to 2.5 wt. % in a suitable solvent. Since it is known that thiol-containing compounds readily improve the corrosion inhibiting properties of other traditional corrosion inhibitor molecules, a second set of formulations were prepared to illustrate this effect. To this end, additional formulations were prepared by dissolving a 2.5 wt % solution of sulfide formyl derivative with 7.5 wt % solutions of quaternary amine based corrosion inhibitors in a suitable solvent. The performance of these two sets of corrosion inhibitor formulations were subsequently tested for performance using a linear polarized resistance test method based on the ASTM G-170 Rotating Cylinder Electrode protocols, the results of which are shown in Table 6.

Linear polarized resistance tests are typically used as a screening method for assessing the corrosion inhibiting ability of additives to a corrosive solution. Compounds of the invention were tested for the ability to act as corrosion inhibitors alone and in combination with other known corrosion inhibitor actives, specifically quaternary ammonium salt compounds.

The following sets of conditions were used to compare the corrosion inhibiting ability of a variety of sulfide formyl derivatives in linear polarized resistance testing:

Temperature: 80° C. (176° F.)

Brine: Synthetic seawater brine

Water cut: 100%

$pCO_2$: atmospheric pressure

Duration: 24 hours

Metal Coupon: C1018 Mild Steel

Linear polarized resistance tests were performed in accordance with ASTM G-170 Rotating Cylinder Electrode standard methods. Briefly, metal coupons, otherwise known as working electrodes, are affixed to a probe and electrically connected to a working and counter electrode through a potentiostat. The electrodes are immersed into the test brine to measure corrosion rates and are calculated as per standard practice and outlined in standards ASTM G3 and ASTM G102.

A number of sulfide formyl derivatives were compared to that of an organic thiol, namely 2-mercaptoethanol, commonly used for corrosion protection of internal oilfield production equipment from both $CO_2$ and $H_2S$ acid corrosion. Performance testing of Ex. W-Y is ongoing

TABLE 6

Linear Polarized Resistance Data (mpy) of Amino-thio-hemiformyls and quats

| Reference Compound | Example | Dose (ppm) | Baseline (mpy) | Corrosion Rate at Equilibrium mpy | % Prot. |
|---|---|---|---|---|---|
| TGA (comparative) | — | 40 | 411.1 | 21.4 | 94.8 |
| 2ME (comparative) | — | 40 | 434.8 | 22.3 | 94.9 |
| Diethanolamine:2ME-FA | Ex. R | 40 | 400.6 | 89.4 | 77.7 |
| Morpholine:2ME-FA | Ex. S | 40 | 390.2 | 56.6 | 85.5 |
| Diethylamine:2ME-FA | Ex. T | 40 | 396.0 | 55.3 | 86.0 |
| Monoethanol amine:2ME-FA | Ex. U | 40 | 383.5 | 37.4 | 90.3 |
| Diethylenetriamine:2ME-FA | Ex. V | 40 | 392.1 | 44.6 | 88.6 |

Example 5: Headspace Tests

Headspace testing was performed according to the method described in Example 3. The results of headspace evaluation experiments are shown in Table 7. The compounds of Ex. R-Y exhibit increased stability to release of hydrogen sulfide upon storage as compared to comparative compounds.

TABLE 7

Headspace Results Amino-thio-hemiformyl

| Reference | Reference Cmp. | Solvent | Headspace Evaluation (ppm) |
|---|---|---|---|
| TGA (comparative) | Comparative | Methanol:Water | >240 |
| TGA (comparative) | Comparative | EGMBE | 200 |
| 2ME (comparative) | Comparative | Methanol:Water | 50 |
| 2ME (comparative) | Comparative | EGMBE | >240 |
| Diethanolamine:2ME-FA | Ex. R | Methanol:Water | <5 |
| Diethanolamine:2ME-FA | Ex. R | EGMBE | 0 |
| Morpholine:2ME-FA | Ex. S | Methanol:Water | 0 |
| Morpholine:2ME-FA | Ex. S | EGMBE | 0 |
| Diethylamine:2ME-FA | Ex. T | Methanol:Water | 0 |
| Diethylamine:2ME-FA | Ex. T | EGMBE | 0 |
| Monoethanol amine:2ME-FA | Ex. U | Methanol:Water | 0 |
| Monoethanol amine:2ME-FA | Ex. U | EGMBE | 0 |
| Diethylenetriamine:2ME-FA | Ex. V | Methanol:Water | <5 |
| Diethylenetriamine:2ME-FA | Ex. V | EGMBE | <5 |
| 2ME:Acetaldehyde | Ex. W | Methanol:Water | <5 |
| Diethanolamine:2ME:Acetaldehyde | Ex. X | Methanol:Water | 0 |
| Diethanolamine:2ME:Acetaldehyde | Ex. X | EGMBE | <5 |
| Piperazine:2ME:FA | Ex. Y | Methanol:Water | <5 |
| Piperazine:2ME:FA | Ex. Y | EGMBE | 0 |

When introducing elements of the invention or the preferred embodiments(s) thereof, the articles "a", "an", "the" and "said" are intended to mean that there are one or more of the elements. The terms "comprising", "including" and "having" are intended to be inclusive and mean that there can be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

What is claimed is:

1. A method of inhibiting corrosion at a surface, the method comprising:
contacting the surface with an effective amount of an anti-corrosion composition, wherein the surface is part of equipment used in the production, transportation, storage, and/or separation of crude oil or natural gas; the composition comprising:
a compound of formula (IA)

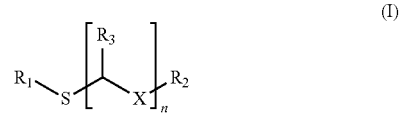

wherein
$R_1$ is alkyl, aryl, or alkenyl;
n is an integer from 1 to 10;
$R_2$ is hydrogen, alkyl, alkenyl, or aryl; and
$R_3$ is hydrogen, alkyl, alkaryl, aryl, or heterocyclo.

2. The method of claim 1, wherein the anti-corrosion composition comprises the compound of formula (IA).

3. The method of claim 2, wherein $R_1$ of Formula (IA) is either:
$C_1$-$C_{24}$ alkyl, $C_1$-$C_{24}$ alkenyl, $C_6$-$C_{12}$ aryl, or $C_3$-$C_8$ cycloalkyl, wherein said alkyl, alkenyl, aryl, or cycloalkyl are each independently unsubstituted or substituted with 1 to 3 substituents independently selected from —F, —Cl, —$NO_2$, —CN, —OH, —$NH_2$, $C_1$-$C_6$ haloalkyl, $C_1$-$C_6$ alkoxy, —$CO_2R_{10}$, and —$CON(R_{11})_2$, wherein $R_{10}$ and $R_{11}$, at each occurrence, are each independently hydrogen or $C_1$-$C_6$ alkyl; or optionally one or more of the —$CH_2$— groups of $R_1$ is replaced with a —C(O)O— group; or
$C_1$-$C_{18}$ alkyl, or $C_3$-$C_8$ cycloalkyl, wherein said alkyl, or cycloalkyl are each independently unsubstituted or substituted with 1 to 3 substituents independently selected from —OH, $C_1$-$C_6$ alkoxy, or —$CO_2R_{10}$, wherein $R_{10}$ at each occurrence, is independently hydrogen or $C_1$-$C_6$ alkyl; or optionally one or more of the —$CH_2$— groups of $R_1$ is replaced with a —C(O)O— group.

4. The method of claim 2, wherein $R_1$ of Formula (IA) is $C_1$-$C_{18}$ alkyl or $C_3$-$C_8$ cycloalkyl.

5. The method of claim 4, wherein $R_2$ of Formula (IA) is hydrogen.

6. The method of claim 5, wherein n of Formula (IA) is 1 to 5.

7. The method of claim 6, wherein $R_3$ of Formula (IA) is hydrogen, methyl, ethyl, propyl, or phenyl.

8. The method of claim 1, wherein the anti-corrosion composition further comprises one or more additional corrosion inhibitors, solvents, asphaltene inhibitors, paraffin inhibitors, scale inhibitors, emulsifiers, water clarifiers, dispersants, emulsion breakers, gas hydrate inhibitors, biocides, pH modifiers, or surfactants.

9. The method of claim 1, wherein the anti-corrosion composition comprises from about 0.1 to about 20 wt. % of one or more compounds of formula (IA) in a 1:1 water: glycol ether solvent system.

10. The method of claim 2, wherein $R_1$ of Formula (IA) is $C_1$-$C_{12}$ alkyl optionally substituted with 1 to 3 substituents of —OH or —$CO_2H$; or $R_1$ is $C_1$-$C_{12}$ alkyl wherein one or more of the —$CH_2$— groups is replaced with a —C(O)O— group.

11. The method of claim 2, wherein $R_1$ of Formula (IA) is $C_1$-$C_{12}$ alkyl substituted with 1 to 3 substituents of —OH or —$CO_2H$; or $R_1$ is $C_1$-$C_{12}$ alkyl wherein one or more of the —$CH_2$— groups is replaced with a —C(O)O— group.

12. The method of claim 2, wherein $R_1$ of Formula (IA) is linear $C_1$-$C_{10}$ alkyl substituted with a terminal —OH group.

13. The method of claim 2, wherein $R_1$ of Formula (IA) is linear $C_1$-$C_{10}$ alkyl substituted with a terminal —$CO_2H$ group.

14. The method of claim 2, wherein $R_1$ of Formula (IA) is linear $C_1$-$C_{10}$ alkyl wherein one of the —$CH_2$— groups is replaced with a —C(O)O— group.

15. The method of claim 2, wherein $R_1$ of Formula (IA) is —$CH_2$—$CH_2$—OH, cyclohexyl, —$(CH_2)_6$—OH, propyl, dodecyl, —$CH_2CH(OH)CH_2OH$, —$CH(C(O)OH)CH_2C(O)OH$, —$(CH_2)_2C(O)OCH_2CH(C_2H_5)C_4H_9$, or —$(CH_2)_2C(O)OH$.

16. The method of claim 2, wherein $R_3$ of Formula (IA) is hydrogen.

17. The method of claim 5, wherein $R_3$ of Formula (IA) is hydrogen.

18. The method of claim 17, wherein $R_1$ of Formula (IA) is —$CH_2$—$CH_2$—OH.

19. The method of claim 17, wherein $R_1$ of Formula (IA) is cyclohexyl, propyl,
   dodecyl, —$CH_2CH(OH)CH_2OH$, —$CH(C(O)OH)CH_2C(O)OH$, —$(CH_2)_2C(O)OCH_2CH(C_2H_5)C_4H_9$, or —$(CH_2)_2C(O)OH$.

\* \* \* \* \*